United States Patent
Nakanishi et al.

(10) Patent No.: US 12,408,635 B2
(45) Date of Patent: Sep. 9, 2025

(54) LIVING MARINE RESOURCE PRODUCTION METHOD AND LIVING MARINE RESOURCE PRODUCTION DEVICE

(71) Applicant: Yokogawa Electric Corporation, Tokyo (JP)

(72) Inventors: Hirofumi Nakanishi, Tokyo (JP); Satoshi Yoshitake, Tokyo (JP); Hiroshi Ikeda, Yokohama (JP); Hisashi Koaizawa, Ichihara (JP)

(73) Assignee: Yokogawa Electric Corporation, Tokyo (JP)

( * ) Notice: Subject to any disclaimer, the term of this patent is extended or adjusted under 35 U.S.C. 154(b) by 1070 days.

(21) Appl. No.: 17/255,339

(22) PCT Filed: Jun. 14, 2019

(86) PCT No.: PCT/JP2019/023704
§ 371 (c)(1),
(2) Date: Dec. 22, 2020

(87) PCT Pub. No.: WO2020/004078
PCT Pub. Date: Jan. 2, 2020

(65) Prior Publication Data
US 2021/0259174 A1 Aug. 26, 2021

(30) Foreign Application Priority Data
Jun. 27, 2018 (JP) .................... 2018-122104

(51) Int. Cl.
*A01K 61/10* (2017.01)
*A01K 61/20* (2017.01)

(52) U.S. Cl.
CPC .............. *A01K 61/10* (2017.01); *A01K 61/20* (2017.01)

(58) Field of Classification Search
CPC ......... A01K 61/10; A01K 61/20; Y02A 40/81
See application file for complete search history.

(56) References Cited

FOREIGN PATENT DOCUMENTS

| | | | |
|---|---|---|---|
| JP | 63-222631 A | | 9/1988 |
| JP | 64-023889 A | | 1/1989 |
| JP | 03-056122 A | | 3/1991 |
| JP | H0356122 A | * | 3/1991 |
| JP | H0824507 B2 | * | 3/1996 |
| JP | 09-019235 A | | 1/1997 |
| JP | H0919235 A | * | 1/1997 |
| JP | H11253067 A | * | 3/1998 |
| JP | 2000-027748 A | | 1/2000 |
| JP | 2001292659 A | * | 10/2001 |
| JP | 2001336479 A | * | 12/2001 |
| JP | 2003333955 A | * | 11/2003 |
| JP | 2004-344015 A | | 12/2004 |
| JP | 2005143403 A | * | 6/2005 |

(Continued)

*Primary Examiner* — Peter M Poon
*Assistant Examiner* — Hae Rie Jessica Byun
(74) *Attorney, Agent, or Firm* — Sughrue Mion, PLLC

(57) ABSTRACT

A deep water drawing step of drawing deep water that exists in a deep region of the sea to a surface region of the sea with an upwelling pipe (1); and a phytoplankton culturing step of culturing the phytoplankton in the upwelling pipe (1) are included to produce, as a basic producer of a food chain, a living marine resource, such as fishes and shellfishes, with phytoplankton produced in the phytoplankton culturing step.

12 Claims, 14 Drawing Sheets

(56) References Cited

FOREIGN PATENT DOCUMENTS

| | | | | |
|---|---|---|---|---|
| JP | 4023772 B2 | * | 12/2007 | |
| JP | 2011001945 A | * | 1/2011 | |
| KR | 900000070 Y1 | * | 1/1990 | |
| WO | WO-2011021992 A1 | * | 2/2011 | ............. E02B 1/003 |

* cited by examiner

LIVING MARINE RESOURCE PRODUCTION METHOD AND LIVING MARINE RESOURCE PRODUCTION DEVICE

CROSS REFERENCE TO RELATED APPLICATIONS

This application is a National Stage of International Application No. PCT/JP2019/023704 filed Jun. 14, 2019, claiming priority based on Japanese Patent Application No. 2018-122104 filed Jun. 27, 2018, the entire contents of each of which are herein incorporated by reference in their entireties.

TECHNICAL FIELD

The present invention relates to a living marine resource production method using deep water that exists in a deep region of the sea, and a living marine resource production device using the deep water.

Priority is claimed on Japanese Patent Application No. 2018-122104, filed Jun. 27, 2018, the content of which is incorporated herein by reference.

BACKGROUND ART

In the related art, deep water that exists in a deep region of the sea is rich in nutrient salts such as phosphates and nitrates, and thus it has been proposed to draw and use the deep water. For example, a deep sea water drawing and diffusing device shown in Patent Literature 1 is configured to include an upwelling pipe that is moored by a sinker submerged in the seabed at a depth of 300 to 600 m or more, and an underwater floating body that is connected to an upper end of the upwelling pipe and floats under a water surface of a photic layer shallower than 100 m in depth. Then, in the underwater floating body, the deep water is drawn through the upwelling pipe, surface water is sucked from a suction port thereof, the two types of water are mixed, and the mixed water is discharged from a discharge port thereof to the photic layer as density flow. Therefore, in the photic layer, it is possible to allow phytoplankton to proliferate as a basic producer of a food chain with the nutrient salts in the drawn deep water.

Further, an aquaculture device shown in Patent Literature 2 is configured such that an opening that opens upward is provided in substantially a center of a floating body structure, a skirt hanging down to a deep water region is provided in a peripheral edge of the opening, and a pump for discharging surface water out of the deep water in the opening is provided in an upper portion of the floating body structure. Then, the deep water is gradually raised by discharging the water in a surface layer in the opening with the pump. Therefore, in the opening, it is possible to allow phytoplankton to proliferate with the nutrient salts of the raised deep water, to then allow zooplankton to proliferate, and to culture fishes with the zooplankton as a feed.

Further, a seawater heating device shown in Patent Literature 3 is configured to include a light collection unit that collects sunlight on water, a light guide unit that guides the sunlight collected by the light collection unit to the deep sea and is constituted by an optical fiber cable, and a heating unit that collects the sunlight guided by the light guide unit to convert the sunlight into heat and is provided at a lower portion of a conduit. In this seawater heating device, when the seawater existing at the lower portion of the conduit is heated by the heating unit, the upwelling of the deep water occurs in the conduit. When the upwelled deep water is supplied to the surface water via the conduit, inorganic nutrient salts are supplied to the surface water to create a fish field.

CITATION LIST

Patent Literature

[Patent Literature 1]
Japanese Unexamined Patent Application, First Publication No. 2000-27748
[Patent Literature 2]
Japanese Unexamined Patent Application, First Publication No. 2001-292659
[Patent Literature 3]
Japanese Unexamined Patent Application, First Publication No. 2004-344015

SUMMARY OF INVENTION

Technical Problem

However, in the living marine resource production device of the related art that uses deep water existing in the deep region of the sea, a large amount of power is required to draw the deep water, or when the drawn deep water is supplied to a wide range of surface water, the deep water is diluted and the concentration of nutrient salts required for producing the phytoplankton cannot be secured, which hinders proliferation of the phytoplankton. For example, in Patent Literature 1, the deep water is drawn by an impeller powered by a steam turbine that is driven with temperature difference energy between the deep water and the surface water, and in Patent Document 2, a plurality of pumps are used to discharge the surface water in the opening and to draw the deep water, and thus both of the devices have defects such as increasing in size and cost. Further, in Patent Literature 1 and 3, the drawn deep water was supplied to a wide range of surface water, the concentration of nutrient salts required for producing the phytoplankton could not be secured in the surface water, and the culture of the phytoplankton did not proceed as expected.

Further, in the living marine resource production device of the related art that uses deep water existing in the deep region of the sea, as in any of the above Patent Literature 1 to 3, the phytoplankton is cultured in a surface water region and therefore a large area is necessary, and culture of the phytoplankton is not controlled, which means that it is not possible to stably produce the phytoplankton and to cope with seasonal fluctuations.

Therefore, the present invention has been made to solve the above-described problems, and an object thereof is to provide a living marine resource production device and a living marine resource production method in which phytoplankton can be cultured with a simple structure, at a low cost, and in a small area.

Solution to Problem (1) A living marine resource production method according to one aspect of the present invention is a living marine resource production method in which a living marine resource is produced with phytoplankton as a basic producer of a food chain, the living marine resource production method including: a deep water drawing step of drawing deep water that exists in a deep region of the sea to a surface region of the sea with an upwelling pipe; and a phytoplankton culturing step of culturing the phytoplankton in the upwelling pipe.

(2) In the living marine resource production method according to the above-described (1), in the phytoplankton culturing step, sunlight may be guided into the upwelling pipe and the deep water in the upwelling pipe is irradiated with the sunlight.

(3) In the living marine resource production method according to the above-described (2), in the phytoplankton culturing step, a generation amount of the phytoplankton may be controlled by adjusting a rising flow rate of the deep water in the upwelling pipe and/or an irradiation amount of the sunlight to the deep water.

(4) In the living marine resource production method according to any one of the above-described (1) to (3), irradiation of the deep water in the upwelling pipe with sunlight may be performed by forming at least a part of the upwelling pipe with a light-transmitting pipe having a light-transmitting property and guiding the sunlight focused on the light-transmitting pipe, or may be performed by disposing a light-transmitting rod having a light-transmitting property in the upwelling pipe and in an axial direction thereof and guiding the sunlight focused on the light-transmitting rod.

(5) In the living marine resource production method according to any one of the above-described (1) to (4), in the deep water drawing step, a temperature difference and a salt concentration difference in the upwelling pipe are used, or the deep water may be drawn by a pump.

(6) A living marine resource production device according to one aspect of the present invention is a living marine resource production device which produces a living marine resource with phytoplankton as a basic producer of a food chain, the living marine resource production device including: a deep water drawing means for drawing deep water that exists in a deep region of the sea to a surface region of the sea with an upwelling pipe; and a phytoplankton culturing means for culturing the phytoplankton in the upwelling pipe.

(7) In the living marine resource production device according to the above-described (6), the phytoplankton culturing means may include an irradiation means for guiding sunlight into the upwelling pipe and irradiating the deep water in the upwelling pipe with the sunlight.

(8) In the living marine resource production device according to the above-described (7), the irradiation means may include: a light collecting means for collecting the sunlight; and a light-transmitting pipe that forms at least a part of the upwelling pipe and irradiates an inside of the upwelling pipe with sunlight collected by the light collecting means, or a light-transmitting rod that is disposed in the upwelling pipe and in an axial direction thereof and irradiates the inside of the upwelling pipe with sunlight collected by the light collecting means.

(9) In the living marine resource production device according to the above-described (8), the light-transmitting pipe may have a scattering material that is mixed therein and scatters the sunlight, and/or a reflective material that is disposed on an outer peripheral surface thereof and reflects the sunlight.

(10) In the living marine resource production device according to the above-described (8) or (9), the light-transmitting rod may include a light-receiving portion having an inverted triangular pyramid shape which is provided at an upper end portion thereof, or a light-receiving portion having an inverted triangular pyramid shape which is provided at an upper end portion thereof and accommodates a convex lens.

(11) In the living marine resource production device according to any one of the above-described (6) to (10), the deep water drawing means may use a temperature difference and a salt concentration difference in the upwelling pipe, or may include a pump that draws the deep water.

(12) In the living marine resource production device according to any one of the above-described (6) to (11), the upwelling pipe may be formed of a cylindrical film or a stretchable bellows type pipe, and a reinforcing member that maintains a shape of the upwelling pipe in a cylindrical shape may be provided.

(13) In the living marine resource production device according to the above-described (12), a plurality of the reinforcing members may be provided in the upwelling pipe to be spaced from each other.

(14) In the living marine resource production device according to any one of the above-described (8) to (10), the upwelling pipe may be formed of a cylindrical film or a stretchable bellows type pipe, wherein one or a plurality of reinforcing members that maintain a shape of the upwelling pipe in a cylindrical shape may be provided, wherein the reinforcing member may include: a large-diameter ring member provided along an inner circumference of the upwelling pipe; a small-diameter ring member provided inside the large-diameter ring member in a radial direction; and a spoke member that connects the large-diameter ring member and the small-diameter ring member to each other, and wherein the light-transmitting rod may be inserted into at least one of the small-diameter ring members.

(15) In the living marine resource production device according to any one of the above-described (6) to (14), a zooplankton culturing vessel may be provided around an upper opening provided in the upwelling pipe to receive the deep water containing the phytoplankton which flows out from the upper opening and to culture zooplankton.

(16) In the living marine resource production device according to the above-described (15), a net for growing fishes may be stretched around the zooplankton culturing vessel.

(17) In the living marine resource production device according to any one of the above-described (6) to (16), the phytoplankton culturing means may have at least one sensor of a chlorophyll sensor that measures a culture state of the phytoplankton in the upwelling pipe, an illuminance sensor that measures illuminance in the upwelling pipe, and a flow rate sensor that measures a flow rate of the deep water in the upwelling pipe, and adjusts phytoplankton culture conditions based on measurement results of the sensors.

(18) In the living marine resource production device according to any one of the above-described (8) to (10) and (14), the living marine resource production device may further include: an intake blower that takes in outside air; and an air diffuser that is provided under the light-transmitting rod and is formed of a porous body, wherein the light-transmitting rod may have, at an axis thereof, an air passage that sends the air taken in from the intake blower to a lower end of the light-transmitting rod, and wherein the air taken in from the intake blower may be supplied from the air diffuser into the upwelling pipe via the air passage.

(19) In the living marine resource production device according to the above-described (18), the irradiation means may include a housing that has a bottom surface provided with an air chamber to which the air taken in from the intake blower is supplied and a hole into which the light-transmitting rod is inserted, wherein the light-transmitting rod may include an intake hole that allows the air passage and the air chamber to communicate with each other and the air in the air chamber to be taken into the air passage when the light-transmitting rod is inserted into the hole, and wherein the housing may include a flexible member that airtightly closes a gap between an outer peripheral surface of the light-transmitting rod and an inner peripheral surface of the hole when the light-transmitting rod is inserted into the hole.

(20) In the living marine resource production device according to the above-described (6), the upwelling pipe may be formed of a non-light-transmitting member, wherein the upwelling pipe may include: a first portion which is provided at an upper portion of the upwelling pipe and is formed in an inverted triangular pyramid shape whose area increases upward; and a second portion which is connected to a lower portion of the first portion and extends from the surface region to the deep region.

Advantageous Effects of Invention

According to the aspects of the present invention, the phytoplankton is cultured in the upwelling pipe that has the lower opening in the deep water existing in the deep region of the sea and the upper opening in the surface region of the sea, that is, in a state isolated from the sea outside thereof, so that it is possible to efficiently culture the phytoplankton in the deep water which is rich in nutrient salts and is clean.

DESCRIPTION OF EMBODIMENTS

Hereinafter, a living marine resource production device for realizing a living marine resource production method according to the present invention will be described with reference to the drawings.

Figure 1:
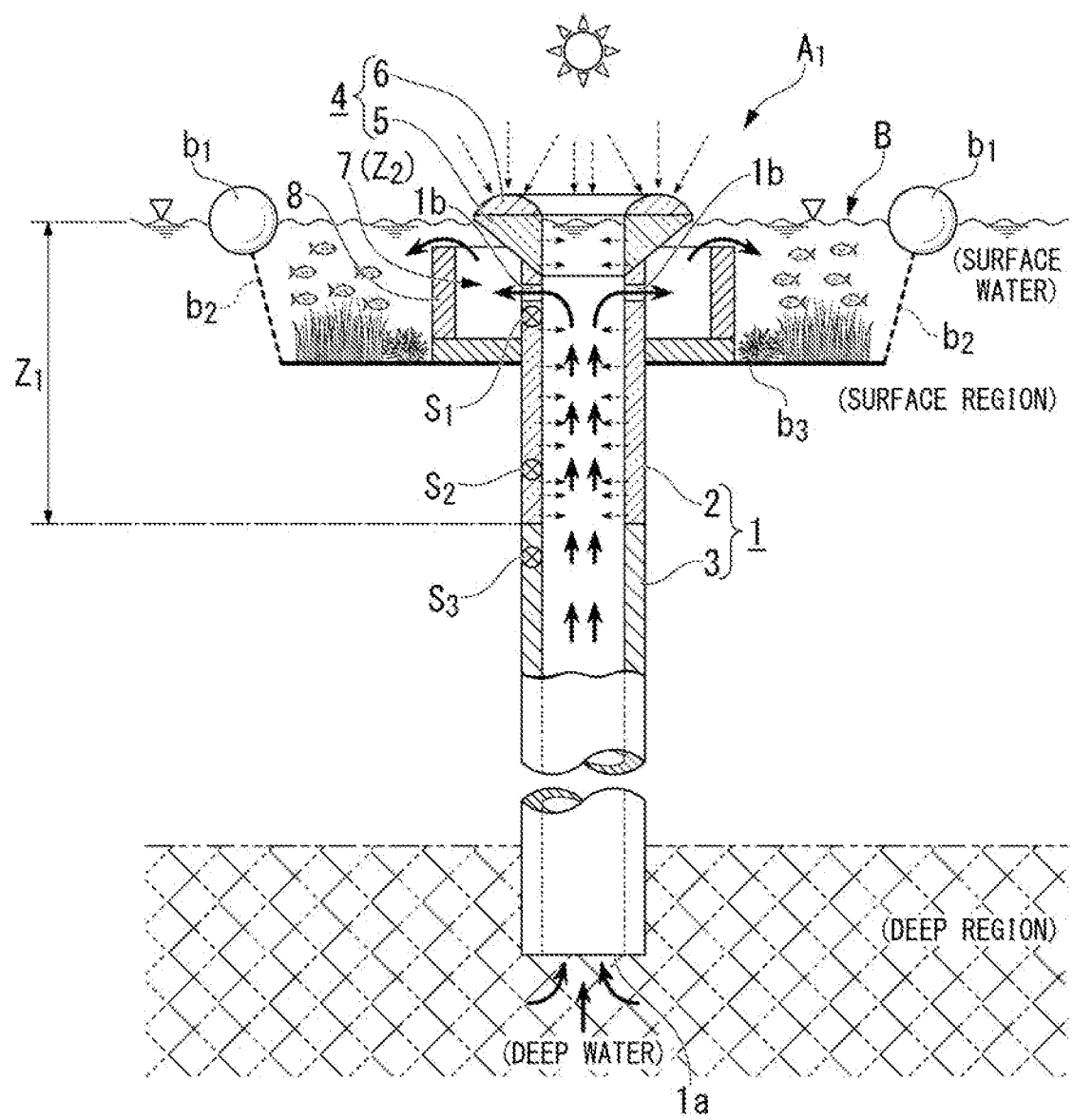
FIG. 1 is a cross-sectional view of a living marine resource production device according to a first embodiment of the present invention.

FIG. 1 is a schematic configuration view of a living marine resource production device $A_1$ according to a first embodiment, and shows an example in which the living marine resource production device is applied to a living resource production region B.

The living marine resource production device $A_1$ is configured to include an upwelling pipe 1 (a deep water drawing means), an irradiation means 4 (a phytoplankton culturing means), and a zooplankton culturing vessel 7.

The upwelling pipe 1 is formed of, for example, a long pipe member made of a synthetic resin. The upwelling pipe 1 extends to near the seabed of the sea at which the living marine resource production device $A_1$ is installed. Specifically, a lower end position of the upwelling pipe 1 is located in deep water existing in a deep region of the sea at which the living marine resource production device $A_1$ is installed, and an upper end position thereof is located at a surface of surface water of a surface region of the sea at which the living marine resource production device is installed.

A lower opening 1a that opens in an axial direction of the upwelling pipe 1 is formed at a lower end of the upwelling pipe, and upper openings 1b that open in a radial direction of the upwelling pipe 1 are formed near an upper end of the upwelling pipe. Normally, the length of this upwelling pipe 1 is several hundreds of meters. Further, the inner diameter of the upwelling pipe 1 is about 1 meter. Then, the ratio (L/D) of the length L of the upwelling pipe 1 to the inner diameter D thereof is made sufficiently large to create an upwelling flow in the upwelling pipe 1.

The upwelling pipe 1 can be divided into a light-transmitting pipe 2 having a light-transmitting property and a non-light-transmitting pipe 3 having a non-light-transmitting property, in the axial direction thereof. The light-transmitting pipe 2 is located on an upper side of the upwelling pipe 1, that is, in the surface region of the sea, and the non-light-transmitting pipe 3 is provided in a form in which it can be joined to a lower end side of the light-transmitting pipe 2. Further, the entire upwelling pipe 1 may be formed by the light-transmitting pipe 2 having a light-transmitting property.

The light-transmitting pipe 2 is made of a material having excellent transparency, is configured to have a constant wall thickness and rigidity, and has an excellent light-guiding property. Therefore, when an upper end surface of the light-transmitting pipe 2 is irradiated with sunlight, the radiating sunlight is guided toward a lower end surface of the light-transmitting pipe 2, and on the way, the radiating sunlight is guided in a circumferential direction of the light-transmitting pipe 2. The length of the light-transmitting pipe 2 is determined by a state of culture and proliferation of phytoplankton, which will be described later, but usually has a length of several tens of meters.

The non-light-transmitting pipe 3 is formed of a synthetic resin material that does not transmit visible light as compared with the light-transmitting pipe 2. Further, it is also possible to form the non-light-transmitting pipe with a material such as a metal that does not transmit visible light. The non-light-transmitting pipe 3 is configured such that an upper end surface thereof is joined to the lower end surface of the light-transmitting pipe 2 and a lower end position thereof is located in the deep water existing in the deep region of the sea.

The non-light-transmitting pipe 3 occupies most of the upwelling pipe 1, which is omitted in the drawing, and has a length excluding the length of several tens of meters of the light-transmitting pipe 2 from the length of several hundreds of meters of the upwelling pipe 1.

A sinker (a weight) that is not shown may be coupled to a lower end of the non-light-transmitting pipe 3 such that the sea currents do not move the living marine resource production device $A_1$ in a case in which the living marine resource production device is installed.

Further, in the illustrated example, the non-light-transmitting pipe 3 is configured to have the same wall thickness as the light-transmitting pipe 2, but to improve transportability and workability and to reduce the manufacturing cost, the non-light-transmitting pipe may be formed of the cylindrical film 3a shown in FIG. 7, which will be described later. The same applies to the non-light-transmitting pipe 3 shown in FIG. 5 which will be described later.

The irradiation means 4 has, as a light collecting means, a light guide body 5 and a lens 6. The light guide body 5 is made of, for example, a synthetic resin and a material having excellent transparency similar to that of the light-transmitting pipe 2. The light guide body 5 is formed in an inverted triangular pyramid shape having a hole having a diameter equal to a hole diameter of the light-transmitting pipe 2 in the center thereof, and is joined to the upper end surface of the light-transmitting pipe 2.

The lens 6 is constituted by convex lenses and is provided to cover the entire upper surface of the light guide body 5. The lens 6 is provided to always be located on a water surface (a sea surface) in a case in which the living marine resource production device $A_1$ is installed. Therefore, when the lens 6 is irradiated with sunlight, the sunlight is focused, and the focused light is guided to the light-transmitting pipe 2 via the light guide body 5.

The upwelling pipe 1 having the above-described configuration is provided with three types of sensors. Among these sensors, a chlorophyll sensor $S_1$ is provided on an upper side of the light-transmitting pipe 2 of the upwelling pipe 1 and is configured to be able to detect a culture state of the phytoplankton in the light-transmitting pipe 2. Further, an illuminance sensor $S_2$ is provided in the light-transmitting pipe 2 and is configured to be able to detect illuminance in the light-transmitting pipe 2. Furthermore, a flow rate sensor $S_3$ is configured to be able to detect the flow rate of the deep water flowing through the upwelling pipe 1.

The zooplankton culturing vessel 7 is constituted by a bottomed cylindrical housing 8 having a predetermined volume around the upwelling pipe 1 of the living marine resource production device $A_1$. The housing 8 is provided to surround the upper openings 1b provided near the upper end of the light-transmitting pipe 2. The upper surface position of the housing 8 is determined to be slightly lower than the position of the water surface (a sea level). The volume of the zooplankton culturing vessel 7 is determined so that the zooplankton can be cultured as prescribed.

Next, the living resource production region B in which the living marine resource production device $A_1$ having the above-described configuration is provided will be described. This living resource production region B is configured to include a buoy $b_1$, a net $b_2$, and a bottom plate $b_3$.

A plurality of buoys $b_1$ are floated on the sea surface centered on the living marine resource production device $A_1$. An upper side of the net $b_2$ that surrounds the living marine resource production device $A_1$ and is provided in a hanging state is coupled to the buoy $b_1$. The mesh of the net $b_2$ is determined such that the fishes that are grown in the net $b_2$ do not escape.

Further, an anchor (not shown) is coupled to the buoy $b_1$ so that the living resource production region B does not flow away with the sea currents.

The bottom plate $b_3$ is configured to be coupled to a lower side of the net $b_2$ and to cover a lower end surface of the living marine resource production device surrounded by the net $b_2$. The upwelling pipe 1 (the light-transmitting pipe 2) of the living marine resource production device $A_1$ is provided to penetrate the bottom plate $b_3$. Further, the zooplankton culturing vessel 7 is provided to be placed on the bottom plate $b_3$.

Hereinafter, the culture of the phytoplankton and the culture of zooplankton using the deep water in the living marine resource production device $A_1$ having the above-described configuration will be described. The "culture" in the present invention includes not only the culture of the phytoplankton or zooplankton, but also the growth and proliferation of the cultured plankton.

First, the solid arrow in FIG. 1 indicates an upwelling state of the deep water in the upwelling pipe 1, that is, the flow of the deep water rising in the upwelling pipe 1. The same applies to FIGS. 5, 6, 16, and 18 that will be described later. Such a rising flow of the deep water results from a temperature difference and a salt concentration difference in the upwelling pipe 1 of which the lower end side is located in the deep water existing in the deep region of the sea and the upper end side is located in the surface water of the surface region of the sea.

The rising phenomenon of deep water in the sea was proposed by marine physicist Henry Melson Stommel et al., and a deep water drawing technique based on this rising phenomenon is also proposed in Japanese Unexamined Patent Application, First Publication No. 2001-336479. Here, it is reported that a rising current of 11 m/day can be obtained with a pipe having a diameter of 1 m and a length of 700 m.

The deep water in the upwelling pipe 1 may be drawn using a pump.

In the living marine resource production device $A_1$, the deep water sucked from the lower opening 1a provided in the non-light-transmitting pipe 3 of the upwelling pipe 1 reaches the light-transmitting pipe 2. In the light-transmitting pipe 2, the sunlight focused by the lens 6 is guided to the light-transmitting pipe 2 via the light guide body 5, and the deep water in the light-transmitting pipe 2 is irradiated with the guided light (refer to the arrow indicated by the chain line in FIG. 1; the same applies to the arrow indicated by the chain line in each of the following figures). Since the irradiated light is sunlight, infrared rays that contribute to the heating of water are included in addition to visible rays required for photosynthesis.

In the deep water in the light-transmitting pipe 2, the phytoplankton is cultured by the radiating light, and in the zooplankton culturing vessel 7, the zooplankton is cultured with the phytoplankton generated in the light-transmitting pipe 2 as a feed. In the living marine resource production device $A_1$, the culture of plankton is separately controlled for each of a first region $Z_1$ and a second region $Z_2$. In this culture, the values from the sensors $S_1$, $S_2$, and $S_3$ described above are used as a reference.

Further, the regions $Z_1$ and $Z_2$ are present in living marine resource production devices $A_2$ to $A_5$ which will be described later, and the explanation thereof will be omitted due to overlap.

Hereinafter, the region $Z_1$, the region $Z_2$, and a living resource production region B will be described separately.

(First Region $Z_1$)

The first region Z covers the entire length of the light-transmitting pipe 2. The deep water that is clean and rich in nutrient salts is introduced into the first region $Z_1$ from the non-light-transmitting pipe 3, and the introduced deep water is irradiated with the light from the light-transmitting pipe 2. In the first region $Z_1$, the deep water is separated from the outside by the light-transmitting pipe 2, and a clean property thereof is maintained. Therefore, in the first region $Z_1$, an environment suitable for photosynthesis is generated under appropriate illuminance and temperature, and the culture of the phytoplankton can be effectively started.

The illuminance of the first region $Z_1$ is set weaker in a lower portion than in an upper portion, and the temperature thereof is set lower in a lower portion than in an upper portion. This is because the lower portion of the first region $Z_1$ is far from the irradiation means 4. In any case, light irradiation to the deep water in the first region $Z_1$ is adjusted to allow sufficient culture of the phytoplankton. Further, the length of the first region $Z_1$ of the light-transmitting pipe 2 is determined such that the culture time can be sufficiently ensured.

The adjustment of the irradiation amount of the light from the light-transmitting pipe 2 to the deep water, that is, the adjustment of the light leakage from the light-transmitting pipe 2, will be described in detail in FIGS. 2 and 3 that will be described later.

The sunlight naturally arrives in the upper portion of the first region $Z_1$. The phytoplankton cultured in the lower portion of the first region $Z_1$ is continuously introduced into the upper portion of the first upper region $Z_1$. In the upper portion of the first region $Z_1$, the upper portion of the light-transmitting pipe 2 is open, and thus there is a risk of contamination from the surface water, however, the deep water keeps the upward flow, and thus the contamination can be effectively prevented.

In the upper portion of the first region $Z_1$, the sunlight arrives naturally and the phytoplankton introduced from the lower portion of the first region $Z_1$ is irradiated with the light from the light-transmitting pipe 2 to be effectively cultured. That is, the upper portion of the first region $Z_1$ is a zone for the phytoplankton to grow and proliferate. Therefore, in the upper portion of the first region $Z_1$, the amount of light to be emitted from the light-transmitting pipe 2 is adjusted such that the phytoplankton can be effectively cultured.

As described above, since the first region $Z_1$ is formed in the light-transmitting pipe 2 in which the irradiation amount of sunlight can be easily adjusted, and the inside of the light-transmitting pipe 2 is a region in which the degree of contamination is lower than the surface water and the water quality is controlled, and which is not easily affected by environmental fluctuations such as weather, it is possible to provide a feature that the generation amount of phytoplankton can be easily controlled. Therefore, in the first region $Z_1$, the phytoplankton as a basic producer of a food chain can be effectively cultured.

(Second Region $Z_2$)

The second region $Z_2$ covers the inside of the zooplankton culturing vessel 7. The deep water containing the phytoplankton generated in the first region $Z_1$ flows into the zooplankton culturing vessel 7 from the upper opening 1b of the upwelling pipe 1. In the zooplankton culturing vessel 7, the inflowing phytoplankton grows further, the grown phytoplankton becomes a feed for the zooplankton, and the zooplankton is effectively cultured.

The zooplankton culturing vessel 7 is easily contaminated because an upper surface thereof is wide open, however, since the inside of the zooplankton culturing vessel 7 is filled with the deep water, the inside of the zooplankton culturing vessel is a region in which the degree of contamination is lower than that of the surface water and the water quality is controlled to some extent. Thus, the inside of the zooplankton culturing vessel is maintained in an environment suitable for phytoplankton and zooplankton culture. Also, the volume of the zooplankton culturing vessel 7, that is, the volume of the second region $Z_2$, is determined to ensure the time for sufficiently culturing the zooplankton with the phytoplankton as a feed.

(Living Resource Production Region B)

The deep water that includes the zooplankton abundantly overflows from the zooplankton culturing vessel 7 into the living resource production region B. The zooplankton that spills into the living resource production region B can serve as a feed for fishes and help the growth of fishes. Moreover, since the deep water that spills into the living resource production region B still contains nutrient salts, it is possible to promote the growth of seaweed.

The living marine resource production device $A_1$ having the above-described configuration can culture the phytoplankton in the light-transmitting pipe 2 of the upwelling pipe 1 that has the lower opening 1a in the deep water existing in the deep region of the sea and the upper opening 1b in the surface region of the sea, that is, in a state isolated from the sea outside thereof. Moreover, since the deep water rising in the upwelling pipe 1 is rich in nutrient salts and clean, the phytoplankton can be efficiently allowed to proliferate. Further, the upwelling pipe 1 can draw the deep water without the need for artificial power such as a pump, and can be realized at a low cost with an extremely simple structure and a small installation area. Further, since the light-transmitting pipe 2 has the chlorophyll sensor $S_1$, the illuminance sensor $S_2$, and the flow rate sensor $S_3$ to detect the state of the inside thereof, the flow velocity, the temperature, the illuminance, or the like suitable for the phytoplankton culture can be controlled by the detection of these sensors $S_1$ to $S_3$, so that the phytoplankton can be efficiently cultured.

Furthermore, in the living marine resource production device $A_1$ having the above-described configuration, the phytoplankton cultured in the light-transmitting pipe 2 is accommodated in the zooplankton culturing vessel 7, so that the zooplankton can be efficiently cultured as a feed for fishes.

Furthermore, in the living marine resource production device $A_1$ having the above-described configuration, the living resource production region B is provided around the zooplankton culturing vessel 7, so that the deep water including the zooplankton can be supplied to the living resource production region B from the zooplankton culturing vessel 7, and thus living marine resources such as fishes, shellfishes, and seaweed can be efficiently produced in the living resource production region B.

Figure 2:
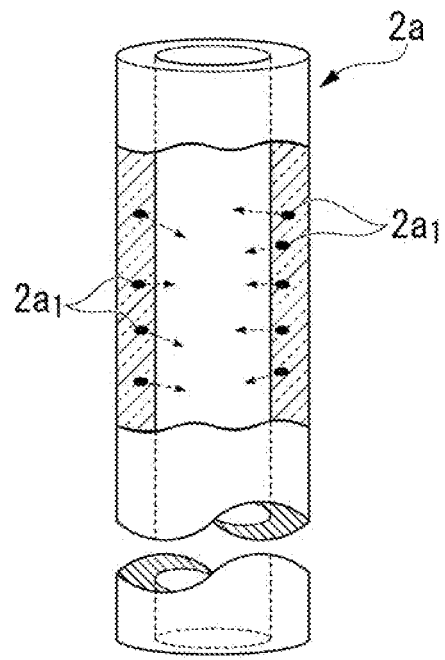
FIG. 2 is a perspective view of a light-transmitting pipe having a different shape from a light-transmitting pipe shown in FIG. 1 with a part thereof shown in a cross section.

FIG. 2 shows a light-transmitting pipe $2a$ different from the light-transmitting pipe 2 shown in FIG. 1. When the light-transmitting pipe $2a$ is manufactured, a scatterer $2a_1$ that reflects light received in the material is mixed in the light-transmitting pipe $2a$. Examples of the scatterer $2a_1$ include inorganic substances and bubbles capable of reflecting light. In the light-transmitting pipe $2a$, it is possible to adjust the light leakage to the deep water in the light-transmitting pipe $2a$ by adjusting the dispersed state or the density difference of the scatterer $2a_1$. Therefore, it is possible to reduce the light leakage at a place near the irradiation means 4 or to increase the light leakage at a place away from the irradiation means 4.

Figure 3:
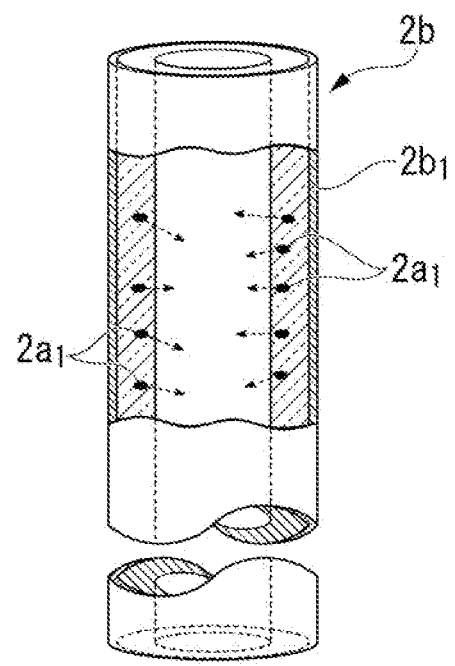
FIG. 3 is a perspective view of a light-transmitting pipe which is an improvement of the light-transmitting pipe shown in FIG. 2 with a part thereof shown in a cross section.

FIG. 3 shows a light-transmitting pipe $2b$ which is an improvement of the light-transmitting pipe $2a$ shown in FIG. 2. An outer periphery of the light-transmitting pipe $2b$ is covered with a reflective material $2b_1$ that reflects light. In this way, the light-transmitting pipe $2b$ of which the outer periphery is covered with the reflective material $2b_1$ can prevent light leakage to the outside of the light-transmitting pipe $2b$ and can efficiently leak the light to the deep water in the light-transmitting pipe $2a$.

Although not shown, as the light leakage adjustment of the light-transmitting pipe, in addition to those shown in FIGS. 2 and 3, the surface of the light-transmitting pipe may be made uneven to change the refractive index of the light.

Figure 4:
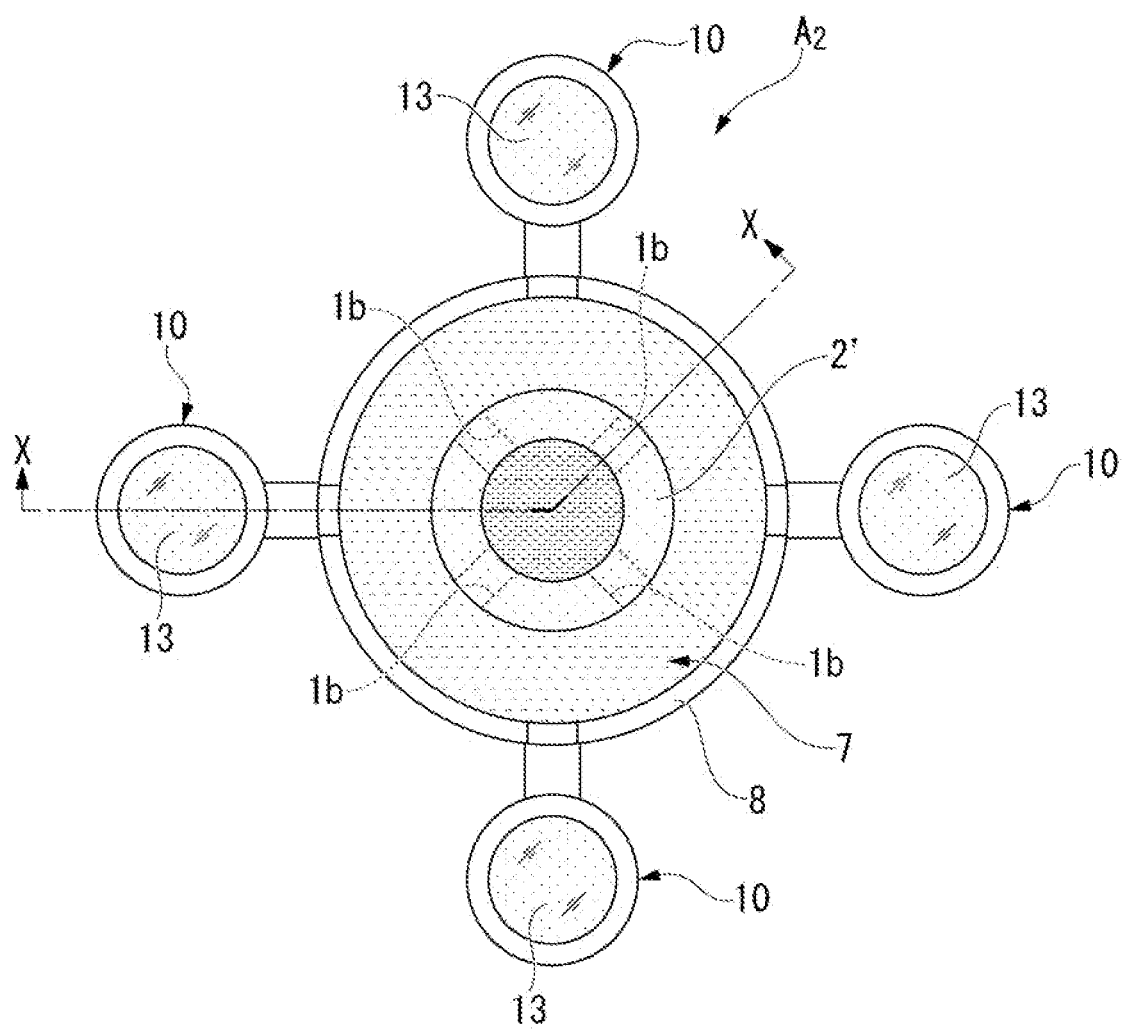
FIG. 4 is a plan view of a living marine resource production device according to a second embodiment of the present invention.
Figure 5:
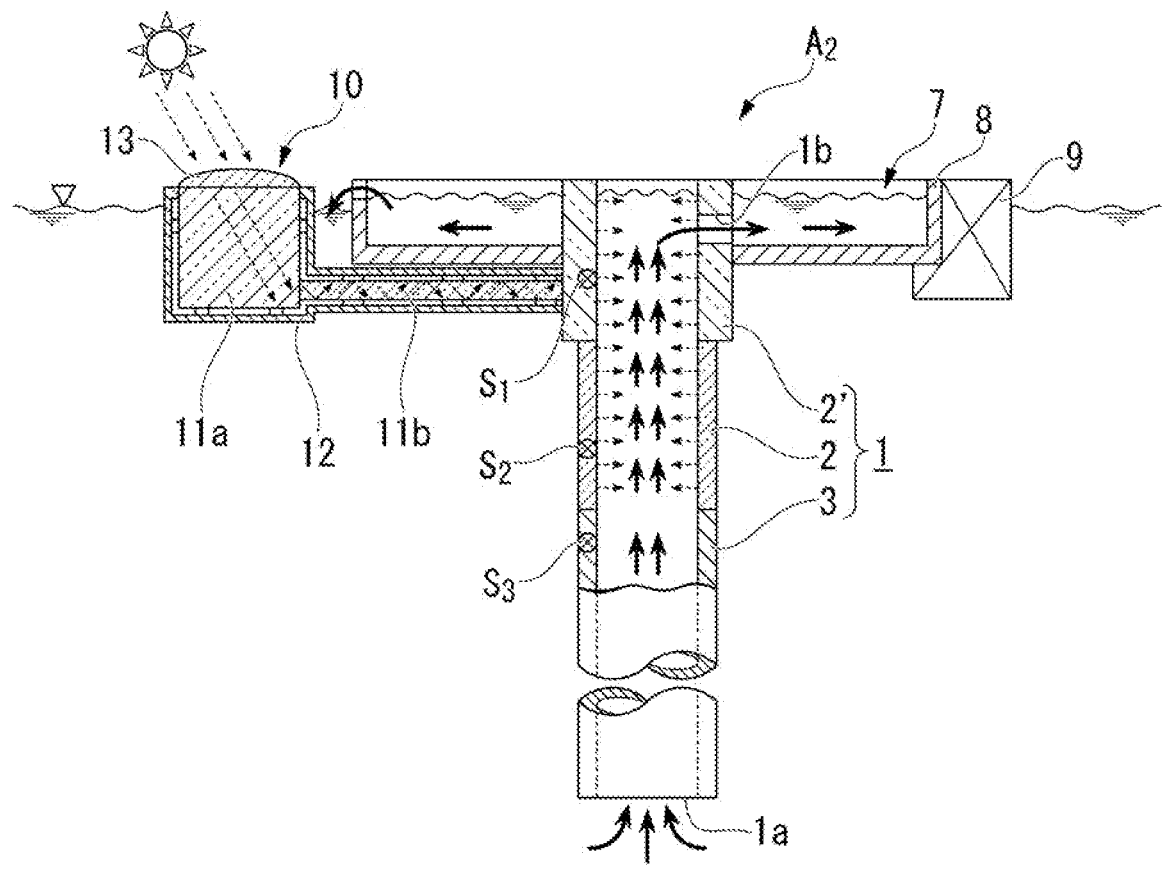
FIG. 5 is a cross-sectional view along line X-X of FIG. 4.

FIGS. 4 and 5 show a living marine resource production device $A_2$ according to a second embodiment of the present invention, FIG. 4 is a plan view, and FIG. 5 is a cross-sectional view along line X-X of FIG. 4. The same reference numerals are used for the same components as those of the above-mentioned living marine resource production device $A_1$, and the description thereof will be omitted due to overlap. The same applies to living marine resource production devices $A_3$ to $A_5$ which will be described later.

The living marine resource production device $A_2$ differs from the living marine resource production device $A_1$ described above in that a plurality of (four in the illustrated example) irradiation means 10 corresponding to the irradiation means 4 of the living marine resource production device $A_1$ are provided. That is, in the living marine resource production device $A_2$, four irradiation means 10 are disposed around the zooplankton culturing vessel 7.

The irradiation means 10 has light guide bodies $11a$ and $11b$, a housing 12, and a lens 13 as a light collecting means. The light guide bodies $11a$ and $11b$ are formed of a light-transmitting material, and are provided in the housing 12 in a watertight manner while maintaining a predetermined space. Of these light guide bodies $11a$ and $11b$, the light guide body $11a$ is located near the outer periphery of the zooplankton culturing vessel 7, and is configured with a lens 13 made of a convex lens joined to an upper surface thereof. The light guide body $11b$ extends in a horizontal direction, one end side thereof is joined to the light guide body $11a$, and the other end side thereof is joined to a thick portion $2'$ of the light-transmitting pipe 2.

In the living marine resource production device $A_2$, a floating body 9 (omitted in FIG. 4) is provided on the outer periphery of the housing 8 of the zooplankton culturing vessel 7. An anchor (not shown) is coupled to the floating body 9 so that the living marine resource production device $A_2$ does not flow away with the sea currents. Such a floating body is also provided in a living marine resource production device $A_3$ which will be described later, but it is omitted.

Since the living marine resource production device $A_2$ having the above-described configuration has the plurality of irradiation means 10, it is possible to use more sunlight and to increase the productivity of the living marine resource more than in the living marine resource production device $A_1$.

The living marine resource production device $A_2$ can be provided in the living resource production region B as in the above-mentioned living marine resource production device $A_1$, but can also be provided independently. In this case, near the outer periphery of the zooplankton culturing vessel 7, small fishes that feed on the zooplankton gather and large fishes that feed on the small fishes gather, so that a rich fish field is formed around the living marine resource production device $A_2$. This effect is the same in living marine resource production devices $A_3$ and $A_4$ which will be described later.

Figure 6:
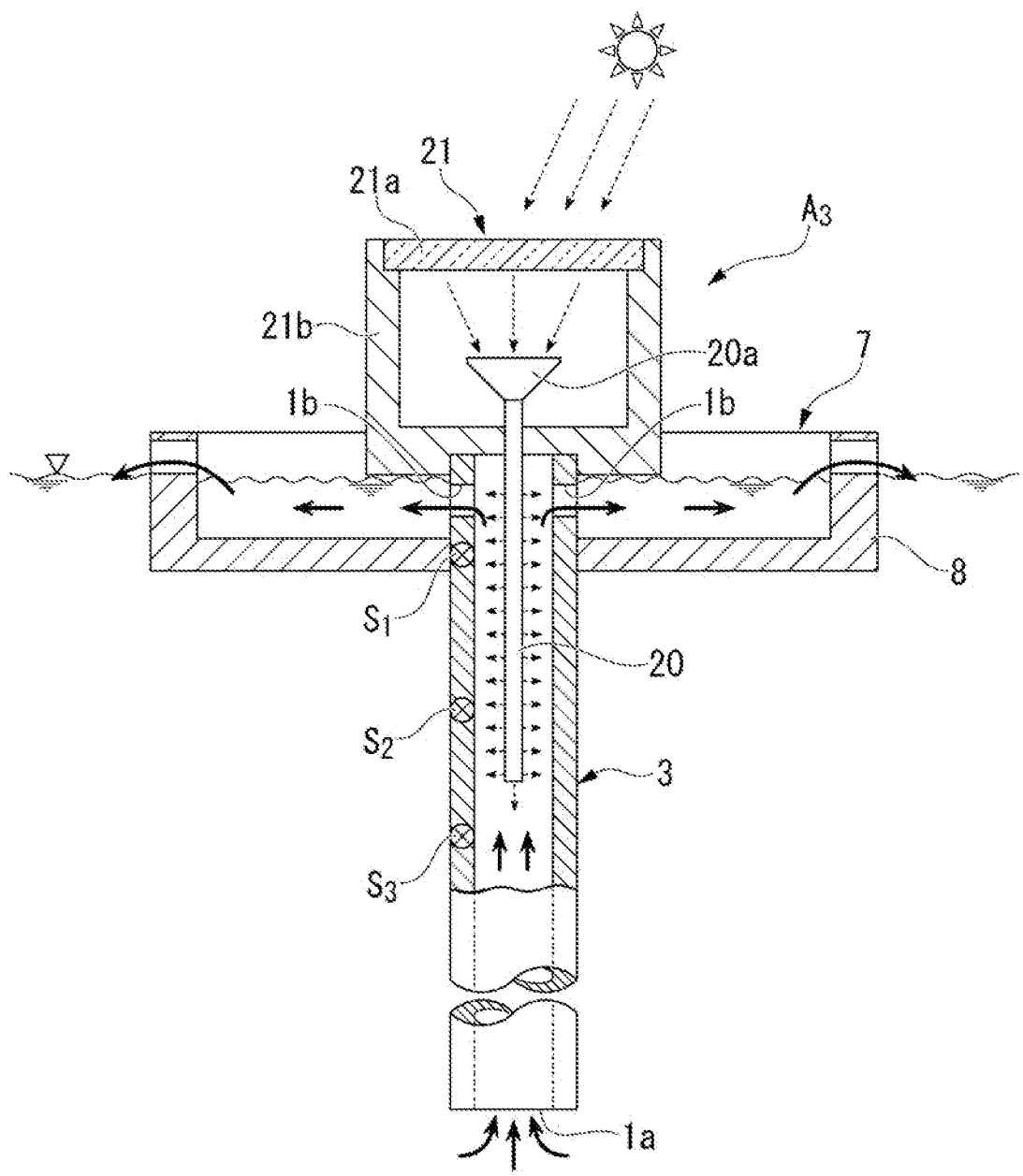
FIG. 6 is a cross-sectional view of a living marine resource production device according to a third embodiment of the present invention.

FIG. 6 is a cross-sectional view of a living marine resource production device $A_3$ according to a third embodiment of the present invention. The living marine resource production device $A_3$ differs from the living marine resource production devices $A_1$ and $A_2$ described above in that the entire upwelling pipe 1 is constituted by the non-light-transmitting pipe 3 and that the light irradiation function of the light-transmitting pipe 2 in the living marine resource production devices $A_1$ and $A_2$ is performed by an irradiation means 21 having a light-transmitting rod 20 at an axial position of the non-light-transmitting pipe 3. In the living marine resource production device $A_3$, the entire upwelling pipe 1 is constituted by the non-light-transmitting pipe 3, so that the upper opening $1b$ is provided on an upper end side of the non-light-transmitting pipe 3.

Figure 7:
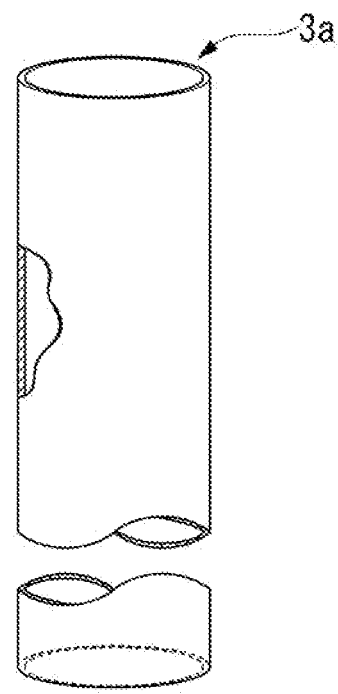
FIG. 7 is a perspective view of a cylindrical film.

The non-light-transmitting pipe 3 used in the living marine resource production device $A_3$ can also be formed of a cylindrical film $3a$ having a thin wall thickness and a non-light-transmitting property as shown in FIG. 7. When the non-light-transmitting pipe 3 is formed of the cylindrical film $3a$, transportability and workability can be improved, and the manufacturing cost can be reduced.

Irradiation of the light introduced into the living marine resource production device $A_3$ is realized by the irradiation means 21 having the light-transmitting rod 20. The irradiation means 21 includes a housing $21b$ which has a lens $21a$ made of a Fresnel lens on an upper surface thereof and has an internal space formed watertightly, and the outside of a bottom surface of the housing $21b$ is joined to the upper end surface of the non-light-transmitting pipe 3 and attached thereto. The lens $21a$ made of the Fresnel lens may be attached to the housing $21b$ with a predetermined inclination such that rainwater or seawater on the surface can be quickly discharged.

Figure 8:
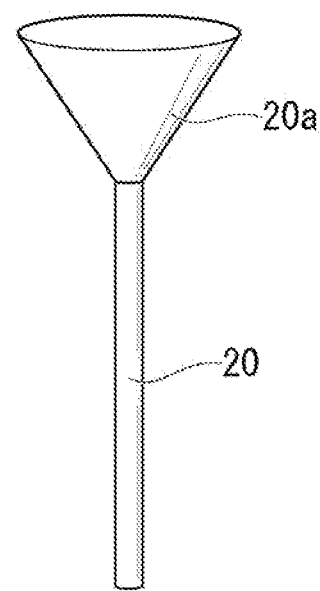
FIG. 8 is a perspective view of a light-transmitting rod.

The light-transmitting rod 20 is formed of, for example, a linear rod made of a synthetic resin having an excellent light-guiding property, and a light-receiving portion $20a$, which has an inverted triangular pyramid shape and is made of a synthetic resin having an excellent light-guiding property, is joined to an upper end portion of the light-transmitting rod, as shown in a perspective view of FIG. 8. The diameter of the light-transmitting rod 20 is determined to avoid resistance of the deep water flowing in the non-light-transmitting pipe 3 and to irradiate the deep water with necessary light. Further, the length of the light-transmitting rod 20 is determined to be substantially equal to the length of the light-transmitting pipe 2 of the above-mentioned living marine resource production devices $A_1$ and $A_2$.

The light-receiving portion 20a guides the sunlight focused by the lens 21a to the light-transmitting rod 20. The light-transmitting rod 20 to which the light-receiving portion 20a is joined is attached to the housing 21b such that a part of the light-receiving portion 20a is located inside the housing, and such that an axial position of the light-transmitting rod 20 matches an axial position of the non-light-transmitting pipe 3.

In the living marine resource production device $A_3$ having the above-described configuration, the light-transmitting rod 20 which is provided in the axial position of the non-light-transmitting pipe 3 can irradiate the deep water flowing in the non-light-transmitting pipe 3, so that it is possible to use the sunlight without waste and to culture the phytoplankton efficiently.

Figure 9:
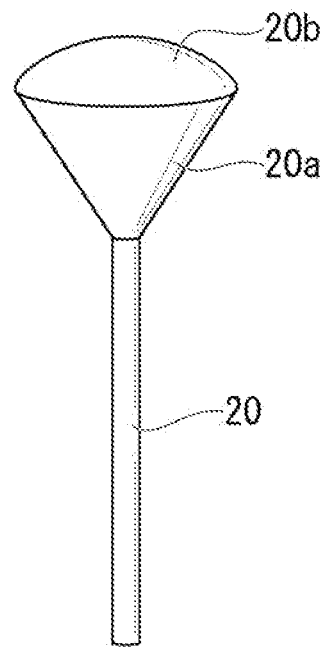
FIG. 9 is a perspective view of a light-transmitting rod having a convex lens.

Further, a convex lens 20b as shown in FIG. 9 can be provided on an upper surface of the light-receiving portion 20a provided at the upper end portion of the light-transmitting rod 20. In this case, the sunlight collected by the lens 20b can be effectively collected in the light-receiving portion 20a. Further, the scatterer $2a_1$ as shown in FIG. 2 described above can be mixed in the light transmitting rod 20, or the surface of the light-transmitting rod can be made uneven, so that it is possible to adjust the light leakage to the deep water.

Figure 10:
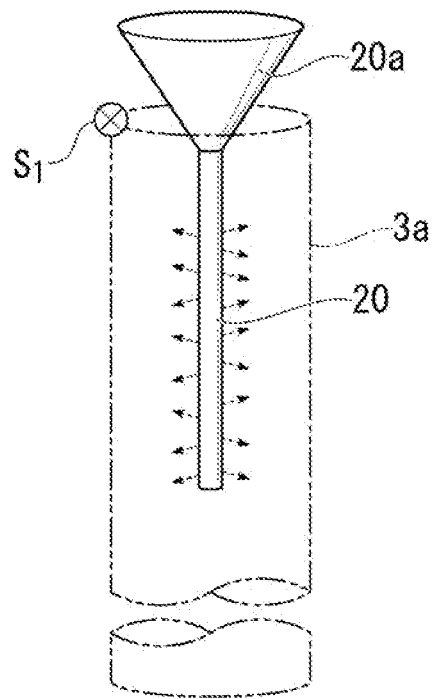
FIG. 10 is a perspective view of a case in which the light-transmitting rod is provided in the cylindrical film.
Figure 11:
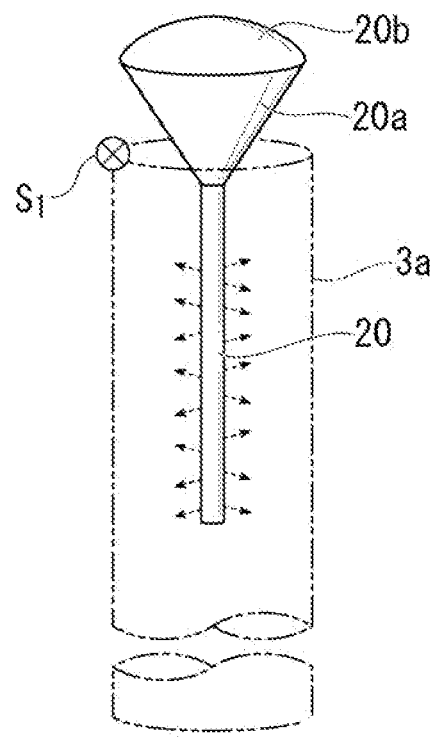
FIG. 11 is a perspective view of a case in which the light-transmitting rod having a convex lens is provided in the cylindrical film.

FIG. 10 shows a perspective view of a case in which the light-transmitting rod 20 is provided in the cylindrical film 3a shown in FIG. 7 described above, and FIG. 11 shows a perspective view of a case in which the light-transmitting rod 20 provided with the convex lens 20b is provided in the cylindrical film 3a. As described above, when the cylindrical film 3a having a thin wall thickness and high flexibility is disposed around the light-transmitting rod 20, transportability and workability can be improved, and the manufacturing cost can be reduced.

Figure 12:
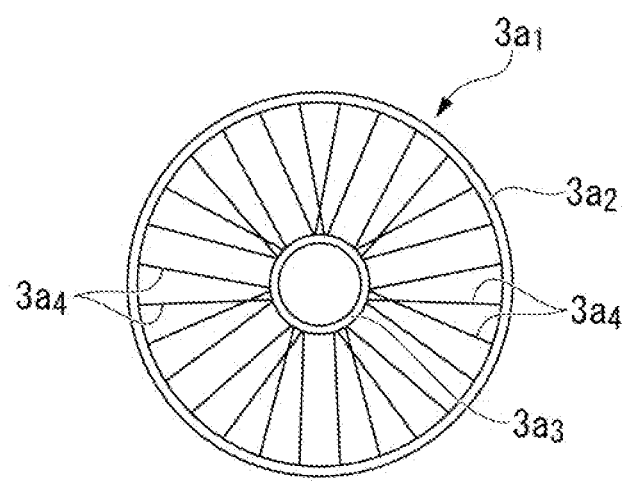
FIG. 12 is a front view of a reinforcing member.

FIG. 12 shows a reinforcing member $3a_1$ of the cylindrical film 3a. The reinforcing member $3a_1$ is used to maintain the cylindrical shape of the cylindrical film 3a. The reinforcing member $3a_1$ is constituted by a rigid large-diameter ring member $3a_2$ having a shape equal to the inner diameter of the cylindrical film 3a, a rigid small-diameter ring member $3a_3$ that is provided at a central portion radially inside the large-diameter ring member $3a_2$, and has a size such that the light-transmitting rod 20 can be inserted into the small-diameter ring member, and a spoke member $3a_4$ connecting between the ring members $3a_2$ and $3a_3$.

A plurality of reinforcing members $3a_1$ having the above-described configuration are disposed inside the cylindrical film 3a in a longitudinal direction to be spaced from each other at a predetermined interval. Therefore, the reinforcing member $3a_1$ can secure the cylindrical shape of the cylindrical film 3a by the large-diameter ring member $3a_2$ provided along an inner circumference of the cylindrical film 3a, and can secure the position of the light-transmitting rod 20 which is disposed in the cylindrical film 3a by at least one small-diameter ring member $3a_3$.

Figure 13:
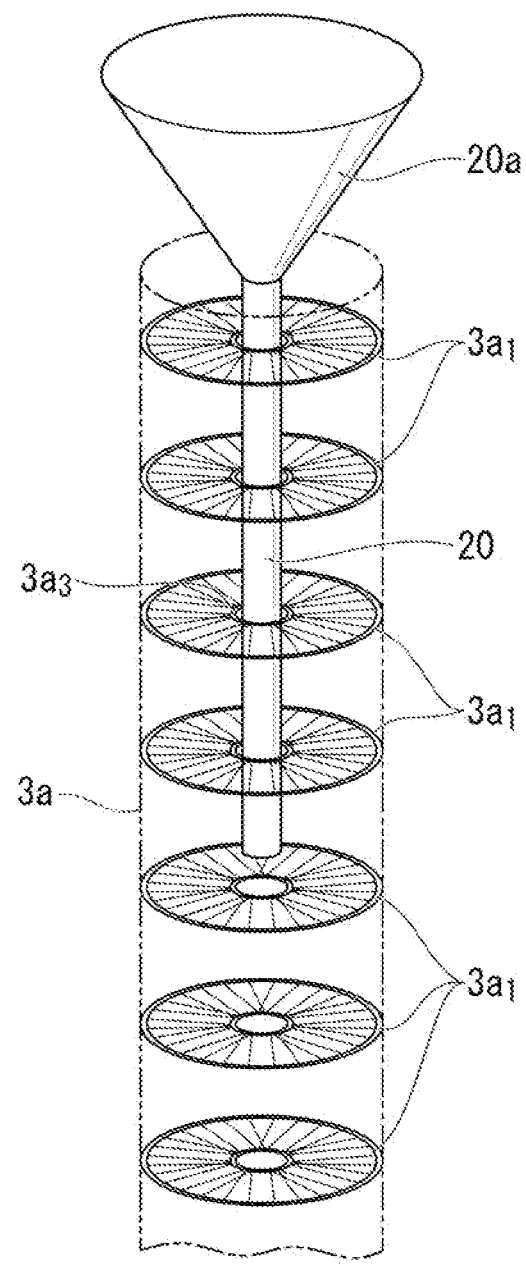
FIG. 13 is a perspective view of a case in which the light-transmitting rod is disposed in a cylindrical film reinforced with the reinforcing member.
Figure 14:
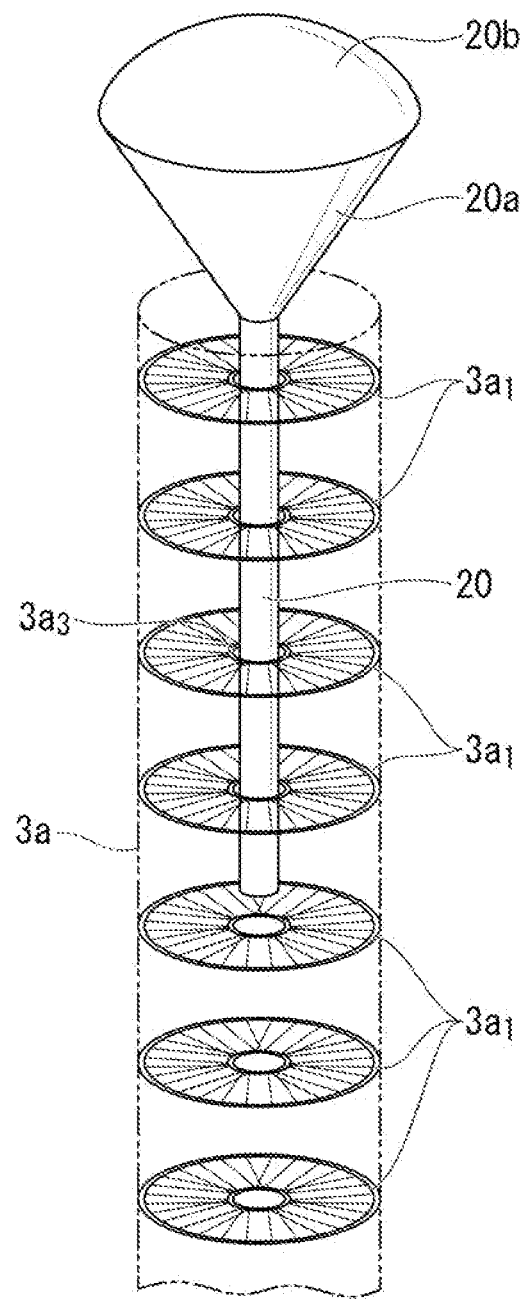
FIG. 14 is a perspective view of a case in which the light-transmitting rod having a convex lens is disposed in a cylindrical film reinforced with the reinforcing member.

FIG. 13 shows a perspective view of a state in which the light-transmitting rod 20 is inserted into the small-diameter ring member $3a_3$ in the cylindrical film 3a reinforced by the reinforcing member $3a_1$, and FIG. 14 shows a perspective view of a state in which the light-transmitting rod 20 provided with the convex lens 20b is inserted into the small-diameter ring member $3a_3$ in the cylindrical film 3a reinforced by the reinforcing member $3a_1$.

Figure 15:
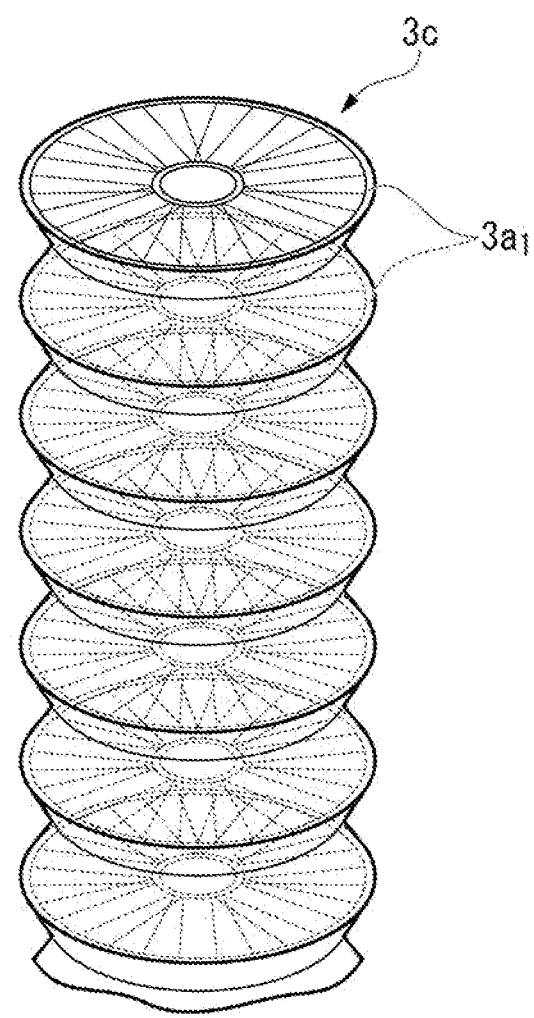
FIG. 15 is a perspective view of a case in which an upwelling pipe is a bellows-shaped non-light-transmitting pipe.

FIG. 15 shows a perspective view of the above-mentioned upwelling pipe 1 as a bellows type pipe 3c having a non-light-transmitting property. The bellows type pipe 3c can be manufactured as a molded product of a synthetic resin.

Also in this bellows type pipe 3c, the reinforcing member $3a_1$ may maintain the cylindrical shape.

When the upwelling pipe 1 is formed as the bellows type pipe 3c, transportability and workability of the upwelling pipe, which usually extends to several hundred meters, can be improved, and the manufacturing cost can be reduced.

Figure 16:
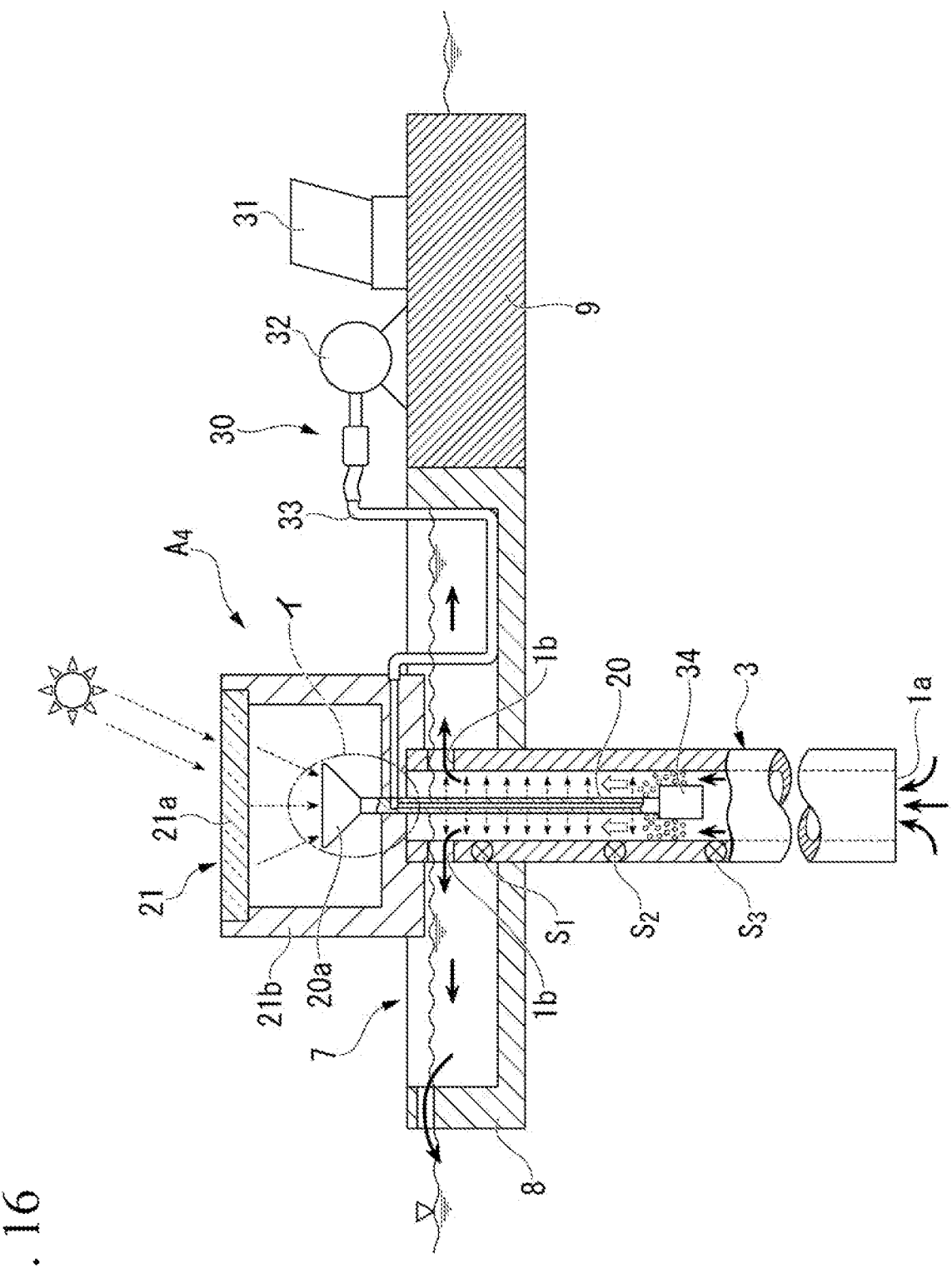
FIG. 16 is a cross-sectional view of a living marine resource production device according to a fourth embodiment of the present invention.

FIG. 16 is a cross-sectional view of a living marine resource production device $A_4$ according to a fourth embodiment of the present invention. The living marine resource production device $A_4$ is characterized in that an air diffusing means 30 is provided in the light-transmitting rod 20 of the living marine resource production device $A_3$ described above.

The air diffusing means 30 is constituted by an intake blower 32 that is driven by the electric power stored by a solar panel 31, an air passage 33, and an air diffuser 34.

The solar panel 31 and the intake blower 32 are provided on the floating body 9 attached to the housing 8 of the zooplankton culturing vessel 7. Then, the compressed air generated by the intake blower 32 is supplied to the air diffuser 34 made of a porous body provided at the lower end portion of the light-transmitting rod 20 via the air passage 33. Further, although not shown, the intake blower 32 is provided with a filter for purifying the air so that the air diffused from the air diffuser 34 does not adversely affect the culture of phytoplankton.

The air passage 33 is constituted by an air hose and an air pipe on the water surface side, and is constituted by a passage provided along the axis of the light-transmitting rod 20 on the light-transmitting rod 20 side. The communication between the passage provided at the axis of the light-transmitting rod 20 and the passage on the water surface side is performed via an air chamber 21ba maintained airtightly by an O-ring 35 provided in the housing 21b, as shown in FIG. 17 in an enlarged manner.

Figure 17:
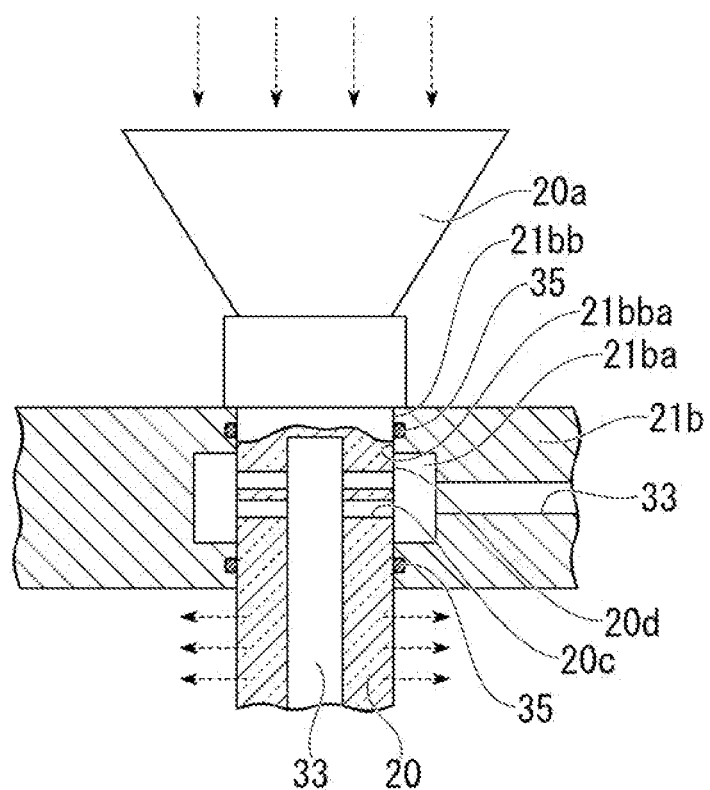
FIG. 17 is an enlarged view of an A part of FIG. 16.

To explain the configuration of FIG. 17 in more detail, the bottom surface of the housing 21b is provided with the air chamber 21ba to which the air taken in from the intake blower 32 is supplied. Further, the bottom surface of the housing 21b is provided with a hole 21bb into which the light-transmitting rod 20 is inserted. The light-transmitting rod 20 includes an intake hole 20c that allows the air passage 33 in the light-transmitting rod 20 and the air chamber 21ba to communicate with each other and the air in the air chamber 21ba to be taken into the air passage 33 in the light-transmitting rod 20 when the light-transmitting rod 20 is inserted into the hole 21bb. The housing 21b includes the O-ring 35 that is a flexible member which airtightly closes a gap between an outer peripheral surface 20d of the light-transmitting rod 20 and an inner peripheral surface 21bba of the hole 21bb when the light-transmitting rod 20 is inserted into the hole 21bb.

In the living marine resource production device $A_4$ having the above-described configuration, air diffusing (bubbling) is performed from the air diffuser 34, so that (1) a $CO_2$ gas in the atmosphere can be introduced, (2) upwelling flow can be formed by the bubbling (see an upward white arrow in FIG. 16), (3) the amount of the atmosphere to be supplied can be supplied to the deep water, (4) accretions on the surface of the light-transmitting rod 20 and the inner surface of the upwelling pipe 1 can be cleaned with bubbles of the bubbling, (5) irradiation light (visible light) and radiant can be uniformized in a cross-sectional direction of the heat upwelling pipe 1 by the bubbling, and (6) the deep water can be stirred by the bubbling. In the living marine resource production device $A_4$, the intake blower 32 requires power, but the power can be obtained via the solar panel 31, so that it is possible to suppress the running cost.

Figure 18:
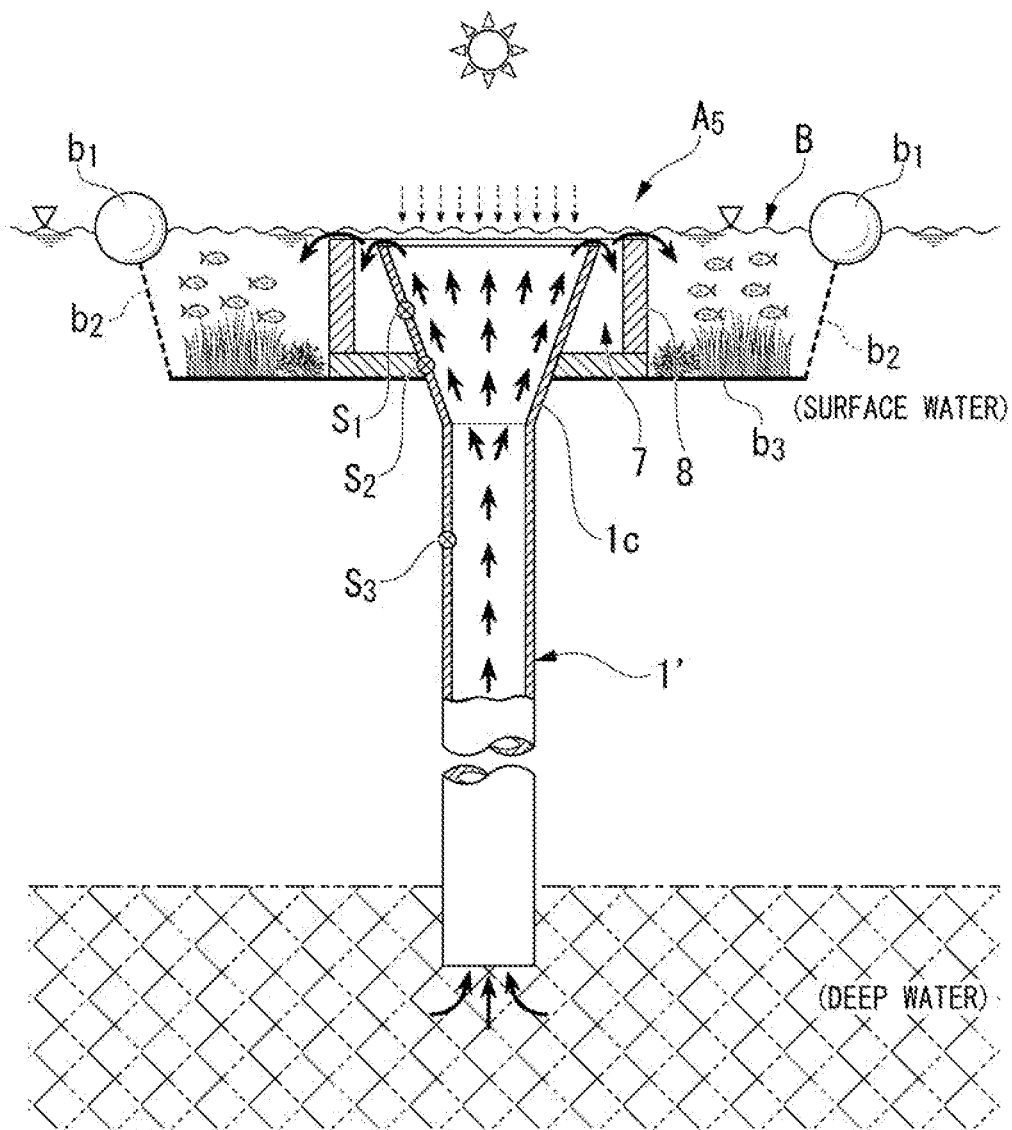
FIG. 18 is a cross-sectional view of a living marine resource production device according to a fifth embodiment of the present invention.

FIG. 18 is a cross-sectional view of a living marine resource production device $A_5$ according to a fifth embodiment of the present invention. The living marine resource production device $A_5$ is characterized in that the upwelling pipe is provided as a trumpet-shaped upwelling pipe 1' with a trumpet portion 1c in which the upper portion of the upwelling pipe is formed in an inverted triangular pyramid shape whose area increases upward, without using the light guiding means of the light-transmitting pipe 2 and the light-transmitting rod 20 as in the living marine resource production devices $A_1$ to $A_4$ described above. The trumpet portion 1c of the upwelling pipe 1' is an example of a "first portion". A portion of the upwelling pipe 1' other than the trumpet portion 1c is an example of a "second portion".

The trumpet-shaped upwelling pipe 1' is formed of a synthetic resin having a non-light-transmitting property, but it can also be formed of a metal. Then, the upwelling pipe 1' is attached to the housing 8 of the zooplankton culturing vessel 7 such that the trumpet portion 1c is located in the housing of the zooplankton culturing vessel.

In the living marine resource production device $A_5$ having the above-described configuration, when the deep water rises in the upwelling pipe 1', the rising speed is gradually lowered in the trumpet portion 1c, the residence time in the trumpet portion 1c becomes longer, and the sunlight is directly received on the large surface area of the trumpet portion 1c. Further, the trumpet portion 1c is easily contaminated because it is located on a surface of the surface water, however, since the inside of the trumpet portion 1c is filled with the deep water, the inside of the trumpet portion is a region in which the degree of contamination is lower than that of the surrounding surface water and the water quality is controlled to some extent. Thus, the inside of the trumpet portion is maintained in an environment suitable for phytoplankton culture. That is, in the trumpet portion 1c, it is possible to culture the phytoplankton in a state of being isolated from the sea outside thereof. Moreover, the living marine resource production device $A_5$ can inexpensively culture the phytoplankton without using the light guiding means of the light-transmitting pipe 2 and the light-transmitting rod 20 as in the living marine resource production devices $A_1$ to $A_4$ described above.

Although the embodiments of the living marine resource production devices according to the present invention have been described above, the present invention is not limited to the above-described embodiments and can be appropriately changed without departing from the spirit of the present invention. Further, it is possible to replace the components in the above-described embodiments with well-known components as appropriate without departing from the spirit of the present invention.

REFERENCE SIGNS LIST

1 Upwelling pipe (deep water drawing means)
1a Lower opening
1b Upper opening
1c Trumpet portion
2 Light-transmitting pipe
2' Thick portion
2a Light-transmitting pipe
$2a_1$ Scatterer
2b Light-transmitting pipe
$2b_1$ Reflective material
3 Non-light-transmitting pipe
3a Cylindrical film
$3a_1$ Reinforcing member
$3a_2$ Large-diameter ring member
$3a_3$ Small-diameter ring member
$3a_4$ Spoke member
3c Bellows type pipe
4 Irradiation means (phytoplankton culturing means)
5 Light guide body
6 Lens
7 Zooplankton culturing vessel
8 Housing
9 Floating body
10 Irradiation means
11a Light guide body
11b Light guide body
12 Housing
13 Lens
20 Light-transmitting rod
20a Light-receiving portion
20b Lens
20c Intake hole
20d Outer peripheral surface
21 Irradiation means
21a Lens
21b Housing
21ba Air chamber
21bb Hole
21bba Inner peripheral surface
30 Air diffusing means
31 Solar panel
32 Intake blower
33 Air passage
34 Air diffuser
35 O ring
$A_1$ to $A_5$ Living marine resource production device
B Living resource production region
$b_1$ Buoy
$b_2$ Net
$b_3$ Bottom plate
$S_1$ Chlorophyll sensor
$S_2$ Illuminance sensor
$S_3$ Flow rate sensor
$Z_1$ First region
$Z_2$ Second region

The invention claimed is:

1. A living marine resource production method in which a living marine resource is produced with phytoplankton as a basic producer of a food chain, the living marine resource production method comprising:
   drawing deep water that exists in a deep region of the sea to a surface region of the sea with an upwelling pipe formed by a light-transmitting pipe and a non-light-transmitting pipe;
   guiding light to the upwelling pipe through a light guide body and a lens, the light guide body having an inverted pyramid shape and a hole with a diameter equal to a diameter of the light-transmitting pipe; and
   culturing the phytoplankton in the upwelling pipe,
   wherein an outer wall of the light-transmitting pipe is coplanar with an outer wall of the non-light transmitting pipe, and
   wherein, in the phytoplankton culturing, when sunlight is irradiated to an upper end surface of the light-transmitting pipe, the irradiated sunlight is guided toward a lower end surface of the light-transmitting pipe, and around a circumference of the light-transmitting pipe.

2. The living marine resource production method according to claim 1, wherein, in the phytoplankton culturing, the sunlight is guided, via the light-transmitting pipe, into the upwelling pipe and the deep water in the upwelling pipe is irradiated with the sunlight.

3. The living marine resource production method according to claim 2, wherein, in the phytoplankton culturing, a generation amount of the phytoplankton is controlled by adjusting a rising flow rate of the deep water in the upwelling pipe and/or an irradiation amount of the sunlight to the deep water.

4. The living marine resource production method according to claim 1, wherein, in the deep water drawing,
the deep water is drawn based on a temperature difference and a salt concentration difference in the upwelling pipe, or the deep water is drawn by a pump.

5. The living marine resource production method according to claim 1, wherein the upwelling pipe has a wall thickness defined between in inner wall and an outer wall thereof, and
wherein the irradiated sunlight is guided through the light-transmitting pipe between the inner wall and the outer wall of the light-transmitting pipe of the upwelling pipe.

6. A living marine resource production method comprising:
drawing deep water from a deep region of the sea to a surface region of the sea with a light-transmitting upwelling pipe that has a light-transmitting property, the light-transmitting upwelling pipe formed by a light transmitting pipe and non-light transmitting pipe;
guiding light to the light-transmitting upwelling pipe through a light guide body and a lens, the light guide body having an inverted pyramid shape and a hole with a diameter equal to a diameter of the light-transmitting upwelling pipe; and
culturing phytoplankton in the light-transmitting upwelling pipe by sunlight that is received into an upper end surface of the light-transmitting upwelling pipe, and guided toward a lower end surface of the light-transmitting upwelling pipe, and around a circumference of the light-transmitting upwelling pipe.

7. The living marine resource production method according to claim 6, wherein the sunlight is guided via the light-transmitting upwelling pipe to irradiate the deep water in the light-transmitting upwelling pipe with the sunlight.

8. The living marine resource production method according to claim 7, further comprising adjusting a rising flow rate of the deep water in the light-transmitting upwelling pipe to control an amount of the phytoplankton that is generated.

9. The living marine resource production method according to claim 8, further comprising adjusting the rising flow rate of the deep water in the light-transmitting upwelling pipe by controlling an amount of the sunlight irradiated onto the deep water.

10. The living marine resource production method according to claim 7, further comprising adjusting a rising flow rate of the deep water in the light-transmitting upwelling pipe by controlling an amount of the sunlight irradiated onto the deep water.

11. The living marine resource production method according to claim 6, wherein the deep water is drawn based on a temperature difference and a salt concentration difference of the deep water in the light-transmitting upwelling pipe.

12. The living marine resource production method according to claim 6, wherein the deep water is drawn by a pump.

* * * * *